United States Patent [19]

Klass et al.

[11] 4,316,961

[45] Feb. 23, 1982

[54] METHANE PRODUCTION BY ANAEROBIC DIGESTION OF PLANT MATERIAL AND ORGANIC WASTE

[75] Inventors: Donald L. Klass, Barrington; Sambhunath Ghosh, Homewood, both of Ill.

[73] Assignee: United Gas Pipe Line Company, Houston, Tex.

[21] Appl. No.: 157,474

[22] Filed: Jun. 9, 1980

[51] Int. Cl.³ .............................................. C12P 5/02
[52] U.S. Cl. .................................. 435/167; 48/197 A; 210/602; 210/603; 435/170; 435/801; 435/822
[58] Field of Search ............... 435/166, 167, 169, 170, 435/244, 252, 801, 822, 277; 210/602, 603, 613, 612; 48/197 A, 197 FM, 209

[56] References Cited

U.S. PATENT DOCUMENTS

| | | | |
|---|---|---|---|
| 1,838,474 | 12/1931 | Buswell et al. | 435/167 X |
| 2,198,737 | 4/1940 | Petersen | 435/167 X |
| 3,994,780 | 11/1976 | Klass et al. | 435/167 |
| 4,022,665 | 5/1977 | Ghosh et al. | 435/801 X |
| 4,252,901 | 2/1981 | Fischer et al. | 435/167 |

FOREIGN PATENT DOCUMENTS 2743618  3/1979  Fed. Rep. of Germany ...... 435/167

OTHER PUBLICATIONS

Nelson et al., "Effect of Temperature of Digestion, Chemical Composition, and Size of Particles on Production of Fuel Gas from Farm Wastes", Journal of Agricultural Research, vol. 58, No. 4, 2-1939.

*Primary Examiner*—Arthur L. Corbin
*Attorney, Agent, or Firm*—Thomas W. Speckman

[57] ABSTRACT

A process for production of methane gas in higher yields and higher rates by thermophilic or mesophilic anaerobic digestion of plant material and/or organic waste in admixture with an extract of different plant material. Increases of methane yield of greater than about 25% and up to about 500% are obtained by addition of the extract of different plant material to a normally low biodegradable plant and/or organic waste material before anaerobic digestion thereof. The resulting methane yields and production rates are higher than those obtained by the sum from anaerobic digestion of the individual components when using the extract as taught by this invention.

11 Claims, No Drawings

METHANE PRODUCTION BY ANAEROBIC DIGESTION OF PLANT MATERIAL AND ORGANIC WASTE

BACKGROUND OF THE INVENTION

1. Field of the Invention

Methane production of anaerobic digestion has been widely practiced, particularly with respect to digestion of sewage sludge organic waste. In recent times, the world-wide energy shortage has furthered consideration and improvement of such non-fossil sources of energy. This invention relates to a process for improved methane production from and beneficiation of anaerobic digestion of plant material and/or organic waste comprising anaerobic digestion of plant material and/or organic waste of normally low biodegradability in the presence of extract of different plant material. The extract is present in about 10 to about 90 volume percent of the digester contents. The process may be carried out under mesophilic or thermophilic temperatures for detention times in excess of about four days. Under steady state anaerobic digestion, the plant material and/or organic waste of normally low biodegradability in the presence of the extract of different plant material results in synergistic action providing higher methane yields and production rates than those that result from the anaerobic digestion of the individual feed components separately.

2. Description of the Prior Art

The production of methane gas by anaerobic digestion of various organic wastes has been known. There have been continuous efforts to improve methane yield resulting from anaerobic digestion. Most of the prior attempts to increase methane yield have been centered around anaerobic digestion as practiced in municipal waste treatment plants as exemplified by U.S. Pat. Nos. 3,640,846, teaching addition of coal; 3,981,800, teaching pressurized digestion; and 4,022,665, teaching two phase digestion of sewage sludge. Other attempts to improve the production rate and yield of methane by anaerobic digestion have related to improved anaerobic digestion by utilization of liberated enzymes of the biomass for contribution to more efficient digestion as taught by U.S. Pat. No. 3,994,780. The U.S. Pat. No. 3,994,780 patent teaches the applicability of its process to a wide variety of organic feeds, but does not suggest the synergistically improved methane production by anaerobic digestion of plant material and/or organic waste of normally low biodegradability in the presence of an extract of different plant material. The anaerobic digestion of terrestrial plant material to produce methane has been recognized as exemplified by D. L. Klass and S. Ghosh, "Methane Production by Anaerobic Digestion of Bermuda Grass", presented at symposium on Biomass as a Non-fossil Fuel Source, ACS/Chem. Soc. of Japan Joint Chemical Congress, Honolulu, Hawaii, Apr. 1-6, 1979. Likewise, the anaerobic digestion of aquatic plant material to produce methane has been recognized as exemplified by R. P. Lecuyer and J. H. Marten, "An Economic Assessment of Fuel Gas from Water Hyacinths", Symposium Papers, Clean Fuels from Biomass, Sewage, Urban Refuse, Agricultural Wastes, Orlando, Fla., Jan. 27-30, 1976. Again, the synergism resulting in improved methane production by anaerobic digestion of plant material and/or organic waste or normally low biodegradability in the presence of an extract of different plant material is not suggested.

Stimulation of methane production in anaerobic waste treatment by metal cations has been recognized as has the problem of toxicity in methane producing anaerobic systems as exemplified by I. J. Kugelman and K. K. Chin, "Toxicity, Synergism and Antagonism in Anaerobic Waste Treatment Processes", Anaerobic Biological Treatment Processes, Advances in Chemistry, Series 105 (1971). While recognizing the sensitivity of methane production in anaerobic waste treatment processes, there is no suggestion of the improvement of anaerobic digestion of plant material and/or organic waste of normally low biodegradability in the presence of an extract of different plant material in methane production. In the past, there have been attempts to increase methane production by the expensive addition of specific chemicals to the digester to overcome various deficiencies.

SUMMARY OF THE INVENTION

The process of this invention provides production of methane gas in higher yields and higher rates by thermophilic or mesophilic anaerobic digestion of plant material and/or organic waste of normally low biodegradability in the presence of an extract of different plant material. The resulting methane yields and production rates are higher than those obtained by the sum from anaerobic digestion of the individual feed components. The plant material may be of terrestrial or aquatic origin. It is particularly preferred that the plant material be a mixture of terrestrial and aquatic plant materials. The practice of this invention utilizes natural materials without the need of expensive isolation techniques or use of chemicals, per se.

The term "plant material" as used in this description and the appended claims includes any of the organisms of the kingdom of Plantae which typically have cell walls composed of cellulose in large part and have nutritive systems in which carbohydrates are formed photosynthetically. The plant material useful in this invention is fresh harvested or stored plant material, which is usually grown on farms for this purpose, and is untreated chemically or physically, except for size reduction. Included are both terrestrial plants and aquatic plants. Terrestrial plants include warm season grasses, such as Bermuda grass and Elephant grass; cool season grasses, such as Kentucky Blue grass and Merion Blue grass; reedy plants, such as Bamboo, rice, cattails, herbaceous plants, such as Kudzu and maze; deciduous trees, such as eucalyptus and poplar; and coniferous trees, such as white and red pines. Exemplary aquatic plants include water hyacinth, duck weed, algae, sea kelp and sargassum.

Normally low biodegradable plants are those which are recalcitrant to gas, particularly methane, production under conventional anaerobic digestion conditions resulting in methane production of less than about 2 SCF/lb. VS added. Included among preferred normally low biodegradable plants are high cellulosics such as Bermuda grass, bamboo, Kentucky blue grass, pine trees, poplar trees, eucalyptus, cattails and mixtures thereof.

By the term "organic waste" as used in this disclosure and the appended claims, we mean all types of organic refuse including sewage sludge, animal waste, municipal waste, industrial waste, forestry waste, agricultural waste, and the like. By forestry waste and agricultural waste we mean to include portions of plants after some physical or chemical treatment, usually not including the entire plant, for example, stumps from logging, sawdust, wood chips, corn stalks, corncob and bagasse. Treatment of municipal solid waste for removal of undesired material such as glass, metals, plastics, stones, and the like, is well known to the art. Included among preferred normally low biodegradable waste are cornstalks and municipal solid waste and mixtures thereof.

It is suitable for the anaerobic digester to include a slurry of plant material and/or organic waste of normally low biodegradability in the presence of an extract of different plant material. The extract comprises about 10 to about 90 volume percent of the total digestion volume, the remainder being water and plant and/or organic waste of normally low biodegradability. Particularly preferred are extract volumes comprising about 15 to about 50 volume percent of digestion volume. The extract is preferably liquid obtained from physical cutting and/or pressing, crushing, steaming, water or solvent extraction and alkali or acid extraction with neutralization. Such methods are well known to one skilled in the art. The extract may be conveniently added to the water used to form a slurry of the normally low biodegradable plant material and/or organic waste. The liquid extract reduces the amount of water required for the slurry. Mixtures of individual plant materials as defined above may be used in both the extract and in the normally low biodegradable fraction. Particularly preferred are mixtures of terrestrial and aquatic plant materials. Preferred extracts are derived from water hyacinth, giant brown kelp, Chlorella, alfalfa, soy bean plants and mixtures thereof. The extract may additionally comprise up to about 10 volume percent sludge liquor, preferably both activated and primary. Preferred amounts of sludge liquor are about 1 to about 5 volume percent, based upon the total digestion volume.

During anaerobic digestion, gas production is principally from the plant and/or organic waste material of normally low biodegradability, only a minor portion, generally on the order of less than 10 percent, of the total gas produced being derived from the extract, even at the higher ranges of volumes of extract set forth above.

Known techniques may be used for anaerobic digestion of the plant and/or organic waste material of normally low biodegradability in the presence of extract of a different plant material. Detention times of in excess of 4 days and preferably about 8 to about 30 days are suitable. Detention times of about 11 to about 16 days are especially preferred. Increases of methane yield of greater than about 25 percent and up to about 500 percent are obtained by addition of extract of different plant material to a normally low biodegradable plant and/or organic waste material for anaerobic digestion. Methane production by anaerobic digestion according to the process of this invention can be continued for long periods of time without addition of external nutrient. Methane production is stable over long periods of digestion. Plant materials, for example herbacious plants such as Giant Reed, bamboo and grasses and woody plants, such as Black Alder, Loblolly Pine, Eucalyptus and Box Elder and organic wastes, such as municipal solid waste and cornstalks, which are recalcitrant to anaerobic digestion alone are readily digested using the process of this invention involving addition of extract of a different plant material. The effluent from the anaerobic digestion according to the process of this invention contains a reduced amount of unconverted residue and has a low concentration of soluble organics indicating low ultimate disposal cost and the feasibility of its recycle to the anaerobic digester with little or no treatment. The digested effluent, although dilute, can be dewatered directly by vacuum filtration or other dewatering method, such as settling or chemical methods, to provide cake-solids content and cake yield comparable to that of filtered, digested sewage sludge.

It is an object of this invention to provide a process for methane production resulting in higher yields and higher production rates than previously obtained by anaerobic digestion of plant and/or organic waste material of normally low biodegradability.

It is another object of this invention to provide a process for methane production by anaerobic digestion of plant and/or organic waste material of normally low biodegradability which does not require addition of external nutrient throughout the process.

It is yet another object of this invention to provide a process for methane production by anaerobic digestion resulting in digester effluent which can be easily dewatered and contains reduced amounts of unconverted residue.

It is still another object of this invention to provide a process for methane production by anaerobic digestion resulting in the digester effluent having low concentration of soluble organics providing easy disposal and recycling to the digester with little or no treatment.

It is another object of this invention to provide a process for methane production from plant and/or organic waste material which is, by itself, recalcitrant to anaerobic digestion.

It is another object of this invention to provide a process suitable for production of synthetic natural gas (SNG) by an anaerobic digestion process comprising anaerobic digestion of plant and/or organic waste material of normally low biodegradability in the presence of an extract of different plant material, thereby allowing better matching of feed supplies for continuous year round operation.

Yet another object of this invention is to provide an organic waste utilizing methane production plant providing simultaneous energy recovery and waste stabilization.

These and other objects and advantages are achieved by the process of this invention as set forth in the more detailed description of preferred embodiments.

DESCRIPTION OF THE PREFERRED EMBODIMENTS

The anaerobic digestion of plant and/or organic waste material of normally low biodegradability in the presence of an extract of different plant material according to this invention, may be carried out under conditions of temperature, both mesophilic (about 20° to 45° C.) and thermophilic (about 45° to 70° C.); detention times in excess of about 4 days and usually about 8 to 30 days, preferably about 11 to 16 days; and loading rates, pretreatment of feed, digester mixing and recycling as known to the art for anaerobic digestion and pointed out more particularly in the references identified above. The present invention may be readily applied to multistage digestion, such as exemplified by our earlier U.S. Pat. No. 4,022,665.

An important aspect of the present invention is the anaerobic digestion of biomass consisting of plant and/or organic waste materials of normally low biodegradability in the presence of an extract of different plant material. The plant and/or organic waste material and extract may be premixed and slurried prior to introduction into the digester or the individual feed materials may be separately introduced into the digester and mixed within the digester. The important aspect is that the mixture of biomass material of normally low biodegradability and extract be together in the active digestion zone. Feeding and associated wasting may be continuous or intermittent.

Any active methane producing mesophilic or thermophilic anaerobic digestion system may be used. Methane-producing anaerobic systems utilizing acid forming bacteria and methane-producing organisms as are well known to be employed to produce methane for sewage sludge can be employed in practice of the present invention. A review of the microbiology of anaerobic digestion is set forth in Anaerobic Digestion, 1. The Microbiology of Anaerobic Digestion, D. F. Toerien and W. H. J. Hattingh, Water Research, Vol. 3, pages 385–416, Pergamon Press (1969). As set forth in that review, the principal suitable non-methanogenic bacteria include species from genera including Aerobacter, Aeromonas, Alcaligenes, Bacillus, Bacteroides, Clostridium, Escherichia, Klebsiella, Leptospira, Micrococcus, Neisseria, Paracolobactrum, Proteus, Pseudomonas, Rhodeopseudomonas, Sarcina, Serratia, Streptococcus and Streptomyces. Exemplary methane-producing organisms suitable for use in the present invention include members of Methanobacterium, Methanococcus and Methanosarcina, specific members being *Methanobacterium formicicum, Methanosarcina barkerii, Methanobacterium omelianskii, Methanococcus vannielii, Methanobacterium sohngenii, Methanosarcina methanica, Methanococcus mazei, Methanobacterium suboxydans* and *Methanobacterium propionicum.* It is usually preferred to use mixed cultures to obtain the most complete fermentation action. Nutritional balance and pH adjustments may be made to the digester system as is known to the art to optimize methane production from the culture used.

Utilization of normally low biodegradable plant and/or organic waste material and extract of a different plant material as a feed for the improved methane producing process of this invention overcomes prior problems of seasonable variability of materials for feed stock. Further, storage of plant material feed stocks has not been satisfactory and is expensive. The use of different plant materials and organic waste according to this invention helps to accommodate the seasonal variability of various species and geographic locations of farms for their production. Utilization of a feed stock including organic waste provides simultaneous energy recovery in the form of methane and waste stabilization in an integrated process. The methane containing gas produced may be treated by methods known to the art to provide substitute natural gas (SNG).

The process of this invention provides a synergistic yield of methane from different plant materials comprising the steps of digesting in an active mesophilic or thermophilic anaerobic digestion system plant and or organic waste material of normally low biodegradability in the presence of an extract of different plant material, each present in greater than an inoculum amount and withdrawing methane-containing gas from the digestion system. By methane-containing gas we mean the mixture of principally methane and carbon dioxide as produced by anaerobic digestion systems. Various means for increasing methane yield, gas quality and digestion kinetics involving feed pretreatment, residue post-treatment and recycling or advanced digestion modes may be used in conjunction with the process of this invention.

The following specific examples are set forth for the purpose of illustration of preferred embodiments and should not limit this invention in any way.

EXAMPLE I

Two digesters were operated under the same conditions, the first being fed only Bermuda grass and the second being fed Bermuda grass plus water hyacinth extract.

Digester start up was achieved with a mixed inoculum, 70 volume percent derived from an existing mesophilic anaerobic digester fed with sea kelp (*Macrocystis pyrifera*) and operated at a loading of 0.1 lb. VS/ft$^3$-day for detention time of 18 days and 30 volume percent derived from another existing mesophilic anaerobic digester fed with mixed primary-activated sewage sludge operated at a loading of 0.8 lb. VS/ft$^3$-day for detention time of 5.6 days. The mixed inoculum contained a diversity of acid forming and methane producing microorganisms as set forth in the Toerien and Hattingh article (Ibid) The digesters were operated with 70 weight percent sea kelp and 30 weight percent sludge on a VS basis with daily feeding and wasting to increase culture volumes by 10% per day to the desired culture volume of about twice the initial inoculum volume. Loading was maintained at 0.1 lb. VS/ft$^3$-day and detention time of 15 days. Each digester then was passed through a feed transition period during which it was fed decreasing amounts of kelp-sludge mixture and increasing amounts of feed materials as follows:

BERMUDA GRASS DIGESTER

Bermuda grass was prepared by reducing the grass to fine particles by fine extrusion cutting to liberate the cellulose fraction of the fibers from the lignin coating. The Bermuda grass was slurried with water for introduction to the digester.

BERMUDA GRASS+EXTRACT OF WATER HYACINTH DIGESTER

Bermuda grass was prepared as above. Water hyacinth plants were chopped, finely ground and pressed under ambient conditions to result in a liquid extract.

An extract additive was made containing:

97 volume percent water hyacinth extract prepared as above;

1 volume percent activated sludge liquor prepared by centrifugation; and 2 volume percent primary sludge liquor prepared by centrifugation.

The daily feed slurry volume contained 18 volume percent, based upon total slurry volume, of the above extract additive.

Each digester was operated in a semicontinuous completely mixed anaerobic digestion mode for a detention time of 12 days, a loading of 0.1 lb. VS/ft$^3$-day, and a temperature of 35° C. at a pH of 6.8–7.1. The run was continued for six detention times and exhibited stable performance. At steady state, the results of each digester were as follows:

|  | Bermuda Grass Digester | Bermuda grass + Extract of Water Hyacinth Digester |
| --- | --- | --- |
| Gas Production Rate vol/day - vol culture | 0.240–0.336 | 0.334–0.544 |
| Average | 0.304 | 0.414 |
| Gas Yield, SCF/lb VS added | 2.40–3.47 | 3.34–5.44 |
| Average | 3.04 | 4.16 |
| Methane Yield, SCF/lb VS added | 1.86 | 2.43 |

It is seen that gas yield increased about 37 percent and methane yield increased about 31 percent by adding 18 volume percent extract of water hyacinth to the digester. This increase is principally due to increased methane and gas production from the Bermuda grass since the theoretical (based upon Volatile Solids content) maximum amount of methane that could be produced from the extract would increase methane yield by only about 5%. The digester effluent had very low concentration of soluble organics and could be dewatered directly by vacuum filtration providing cake-solids content and cake yield comparable to that of filtered, digested sewage sludge.

EXAMPLE II

Two anaerobic digesters were operated with the same feeds as described in Example I, one Bermuda grass and the other Bermuda grass plus 18 volume percent of the daily feed slurry volume water hyacinth extract, as described in Example I, under the same conditions as Example I except the temperature was maintained at 55° C. and loading was 0.5 lb. VS/ft$^3$-day for detention time of 6 days. The results were:

|  | Bermuda Grass Digester | Bermuda grass + Extract of Water Hyacinth Digester |
| --- | --- | --- |
| Gas Production Rate vol/day - vol culture | 1.8 | 2.5 |
| Gas Yield, SCF/lb VS added | 2.8 | 4.0 |
| Methane Yield, SCF/lb VS added | 1.2 | 2.5 |

EXAMPLE III

Two anaerobic digesters are operated under the same conditions as Example I, one with Bermuda grass feed and the other Bermuda grass plug 90 volume percent of the daily feed volume water hyacinth extract as described in Example I resulting in the following gas productions:

|  | Bermuda Grass Digester | Bermuda grass + Extract of Water Hyacinth Digester |
| --- | --- | --- |
| Gas Production Rate vol/day - vol culture | 0.30 | 0.50 |
| Gas Yield, SCF/lb VS added | 3.1 | 5.4 |
| Methane Yield, SCF/lb VS added | 1.9 | 3.3 |

Methane yield increased about 74% due principally to increased methane and gas production from the Bermuda grass since the theoretical maximum amount (based upon Volatile Solids content) of methane that could be produced from the extract would increase methane yield by only about 15%.

EXAMPLE IV

Two anaerobic digesters are operated under the same conditions as Example II except for detention time of 4 days. One digester is fed with Bermuda grass feed and the other Bermuda grass plus 90 volume percent of the daily feed volume water hyacinth extract as described in Example I resulting in the following gas production:

|  | Bermuda Grass Digester | Bermuda grass + Extract of Water Hyacinth Digester |
| --- | --- | --- |
| Gas Production Rate vol/day - vol culture | 1.9 | 2.6 |
| Gas Yield, SCF/lb VS added | 2.6 | 3.8 |
| Methane Yield, SCF/lb VS added | 1.1 | 2.2 |

Methane yield increased about 100% due principally to increased methane and gas production from the Bermuda grass since the theoretical maximum amount (based upon Volatile Solids content) of methane that could be produced from the extract would increase methane yield by only about 10%.

EXAMPLE V

Two anaerobic digesters are operated under the same conditions as Example I, one with Bermuda grass feed and the other Bermuda grass plus 18 volume percent of the daily feed slurry volume being pure water hyacinth juice extract (without sludge liquor as in Example I). The results are:

|  | Bermuda Grass Digester | Bermuda grass + Extract of Water Hyacinth Digester |
| --- | --- | --- |
| Gas Production Rate vol/day - vol culture | .30 | 0.45 |
| Gas Yield, SCF/lb VS added | 3.1 | 4.9 |
| Methane Yield, SCF/lb VS added | 1.9 | 3.0 |

EXAMPLE VI

Two anaerobic digesters were operated under the same conditions as Example II, one with Bermuda grass feed and the other Bermuda grass plus 18 volume percent of the daily feed slurry volume being pure water hyacinth juice extract (without sludge liquor extract as in Example II). The results are:

|  | Bermuda Grass Digester | Bermuda grass + Extract of Water Hyacinth Digester |
| --- | --- | --- |
| Gas Production Rate vol/day - vol culture | 1.8 | 2.4 |

|  | Bermuda Grass Digester | Bermuda grass + Extract of Water Hyacinth Digester |
|---|---|---|
| Gas Yield, SCF/-lb VS added | 2.8 | 3.8 |
| Methane Yield, SCF/-lb VS added | 1.2 | 2.2 |

EXAMPLE VII

Two anaerobic digesters were operated under the conditions set forth in Example I with the feed to one being an aqueous slurry of municipal solid waste and the second a slurry of municipal solid waste in aqueous water hyacinth extract prepared as described in Example I. The municipal solid waste and water hyacinth extract were present in equal weight amounts. The municipal solid waste was air separated and reduced to fine organic-rich particles by two-stage hammermilling. The treated municipal solid waste was comprised of about 87.4 percent paper and paper products; 4.4 percent plastics; 1.3 percent green garbage; and 6.9 percent miscellaneous including food waste and paper pieces difficult to identify, all on a weight percent basis. The results were:

|  | Municipal Solid Waste Digester | Municipal Solid Waste + Extract of Water Hyacinth Digester |
|---|---|---|
| Gas Production Rate vol/day - vol culture | 0.1 | 0.5 |
| Gas Yield, SCF/-lb VS added | 1.0 | 6.0 |
| Methane Yield, SCF/-lb VS added | 0.5 | 3.3 |

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. In a process for improved methane production by anaerobic digestion, the improvement comprising: prior to said digestion, mixing organic material of normally low biodegradability, selected from the group consisting of plant material, organic waste and mixtures thereof, with an extract of plant material derived from different plant material than said low biodegradable plant material to be digested, said extract comprising about 10 to about 90 volume percent of the digestion volume; anaerobically digesting said mixture for a detention time greater than about 4 days; and then removing methane containing gas from the digester.

2. The process of claim 1 wherein said extract comprises about 15 to about 50 volume percent of said digestion volume.

3. The process of claim 1 wherein anaerobic digestion is carried out under mesophilic temperatures of about 20° to about 45° C. for detention times of about 8 to about 30 days.

4. The process of claim 1 wherein anaerobic digestion is carried out under thermophilic temperatures of about 45° to about 70° for detention times of about 8 to about 30 days.

5. The process of claim 1 wherein said plane material comprises both terrestrial and aquatic plant materials.

6. The process of claim 1 wherein said organic material of normally low biodegradability comprises organic waste.

7. The process of claim 1 wherein said extract additionally comprises up to about 10 volume percent sludge liquor.

8. The process of claim 7 wherein said sludge liquor comprises activated and primary sludge liquor.

9. The process of claim 1 wherein said organic material of normally low biodegradability is selected from the group consisting of Bermuda grass, bamboo, Kentucky blue grass, pine trees, poplar trees, eucalyptus, cattails, cornstalks, municipal solid waste and mixtures thereof.

10. The process of claim 1 wherein said extract is derived from plant material selected from the group consisting of water hyacinth, giant brown kelp, Chlorella, alfalfa, soy bean plants and mixtures thereof.

11. In a process of methane production by anaerobic digestion, the improvement comprising obtaining a synergistic yield of methane comprising the steps of:

prior to said digestion, mixing organic material of normally low biodegradability, selected from the group consisting of plant material, organic waste and mixtures thereof, with an extract of plant material derived from different plant material than said low biodegradable plant material to be digested, said extract comprising about 10 to about 90 volume percent of the digestion volume;

digesting said mixture for a detention time greater than about four days in an active mesophilic or thermophilic anaerobic digestion system; and then withdrawing methane-containing gas from said digestion system.

* * * * *